(12) United States Patent
Liang et al.

(10) Patent No.: US 10,064,587 B2
(45) Date of Patent: Sep. 4, 2018

(54) DETERMINING RESPONSE LINES FOR IMAGE RECONSTRUCTION

(71) Applicant: Shenyang Neusoft Medical Systems Co., Ltd., Shenyang (CN)

(72) Inventors: Guodong Liang, Shenyang (CN); Guocheng Wu, Shenyang (CN); Nan Li, Shenyang (CN); Jian Zhao, Shenyang (CN)

(73) Assignee: Shenyang Neusoft Medical Systems Co., Ltd., Shenyang, Liaoning (CN)

( * ) Notice: Subject to any disclaimer, the term of this patent is extended or adjusted under 35 U.S.C. 154(b) by 0 days.

(21) Appl. No.: 15/790,510

(22) Filed: Oct. 23, 2017

(65) Prior Publication Data

US 2018/0110482 A1    Apr. 26, 2018

(30) Foreign Application Priority Data

Oct. 24, 2016 (CN) .......................... 2016 1 0925903

(51) Int. Cl.
*G01T 1/29* (2006.01)
*A61B 6/03* (2006.01)
(Continued)

(52) U.S. Cl.
CPC .............. *A61B 6/037* (2013.01); *A61B 6/481* (2013.01); *G01T 1/2985* (2013.01); *G06T 7/50* (2017.01);
(Continued)

(58) Field of Classification Search
CPC ....... A61B 6/037; A61B 6/481; G01T 1/2985; G06T 11/005; G06T 2207/10104; G06T 7/50; G06T 7/74; G06T 7/75
See application file for complete search history.

(56) References Cited

U.S. PATENT DOCUMENTS

| 7,217,928 B2 * | 5/2007 | Crosetto | G01T 1/1642 |
| | | | 250/366 |
| 2010/0032574 A1 * | 2/2010 | Yoshida | G01T 1/2985 |
| | | | 250/362 |

(Continued)

OTHER PUBLICATIONS

Miyaoka Robert S., et al., "Effect of detector scatter on the decoding accuracy of a DOI detector module," Nuclear Science Symposium, 1999. Conference Record.1999 IEEE Oct. 24-30, 1999, Piscataway, NJ, USA, IEEE, US, vol.2, Oct. 24, 1999 (Oct. 24, 1999), pp. 915-919, XP010500621, DOI:10.1109/NSSMIC.1999.845812 ISBN:978-0-7803-5696-2.

(Continued)

*Primary Examiner* — Marcus Taningco
(74) *Attorney, Agent, or Firm* — Fish & Richardson P.C.

(57) ABSTRACT

Methods, systems, and machine-readable storage mediums for determining response lines for reconstructing images are provided. An example imaging method includes: receiving single event signals in a detector module and associated with a single event, determining a crystal in the detector module and corresponding to a maximum single event signal of the single event signals, determining an actual energy weighting factor of the crystal, determining an actual depth position corresponding to the actual energy weighting factor of the crystal according to associations between depth positions of the crystal and respective reference energy weighting factors for the crystal, as an acting position in the detector module for the single event, determining a response line of a coincidence event according to respective acting positions in the detector module for two single events constituting the coincidence event, the two single events including the single event, and reconstructing an image according to the response line.

20 Claims, 7 Drawing Sheets

(51) Int. Cl.
*A61B 6/00* (2006.01)
*G06T 11/00* (2006.01)
*G06T 7/73* (2017.01)
*G06T 7/50* (2017.01)

(52) U.S. Cl.
CPC .................................. *G06T 7/74* (2017.01); *G06T 7/75* (2017.01); *G06T 11/005* (2013.01); *G06T 2207/10104* (2013.01)

(56) References Cited

U.S. PATENT DOCUMENTS

| 2013/0032706 | A1* | 2/2013 | Cho | G01T 1/1647 250/252.1 |
| 2014/0231655 | A1* | 8/2014 | Dueppenbecker | G01T 1/2985 250/366 |
| 2017/0154444 | A1* | 6/2017 | Kobayashi | G06T 11/003 |
| 2017/0285182 | A1* | 10/2017 | Fu | G01T 1/2985 |

OTHER PUBLICATIONS

European Patent Office: European Search Report mailed in corresponding European Patent Application No. 17197959.4 dated Apr. 3, 2018 (7 pages).

* cited by examiner

DETERMINING RESPONSE LINES FOR IMAGE RECONSTRUCTION

CROSS REFERENCE TO RELATED APPLICATIONS

This application claims priority to Chinese Patent Application No. 201610925903.X entitled "IMAGE METHOD AND IMAGE SYSTEM" and filed on Oct. 24, 2016, the entire content of which is incorporated herein by reference.

TECHNICAL FIELD

The present disclosure relates to an imaging method and an imaging system, particularly, for determining response lines for image reconstruction.

BACKGROUND

A Positron Emission Computed Tomography (hereinafter referred to as PET) system is an imaging device. An operating principle of the PET system may be as follows: a radionuclide may be injected into a subject and then decay in the subject to release a positron. The positron may meet a negatron in the subject in a way that an annihilation event occurs and then two gamma-photons along opposite directions in a straight line may be generated. The two gamma-photons can be received by two detector modules respectively at opposite positions within a time window. A coincidence processing module may perform coincidence determination on this pair of gamma-photons and determine crystals in the detector modules into which the gamma-photons are incident by a response line. The response line may refer to a line connecting the crystals into which the two gamma-photons generated by the annihilation event are incident, respectively. Then, an imaging module can reconstruct an image according to information of the response line.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, systems, and machine-readable storage mediums for determining a response line for reconstructing an image, which can increase image resolution and improve image quality of the reconstructed image.

One innovative aspect of the subject matter described in the present disclosure can be embodied in methods that include the actions of receiving single event signals produced in a detector module and associated with a single event; determining a crystal in the detector module and corresponding to a maximum single event signal of the single event signals; determining an actual energy weighting factor of the crystal; determining an actual depth position corresponding to the actual energy weighting factor of the crystal according to associations between depth positions of the crystal and respective reference energy weighting factors for the crystal, as an acting position in the detector module for the single event; determining a response line of a coincidence event according to respective acting positions in the detector module for two single events constituting the coincidence event, the two single events including the single event; and reconstructing an image according to the response line.

The foregoing and other embodiments can each optionally include one or more of the following features, alone or in combination. In some examples, determining the crystal includes: determining position information of the crystal corresponding to the maximum single event signal output by the detector module; and determining the crystal for the single event based on the determined position information. Determining the position information of the crystal can include using one of a centroid method and a one-to-one output system.

In some implementations, the method further includes: determining a respective reference energy weighting factor corresponding to each of a plurality of depth positions of the crystal; and determining the associations between the plurality of depth positions of the crystal and the determined respective reference energy weighting factors. The method can also include: determining, for each of a plurality of crystals in the detector module, respective associations between depth positions of the crystal and reference energy weighting factors corresponding to the depth positions of the crystal; and storing the respective associations for the plurality of crystals in a repository.

In some cases, determining the respective reference energy weighting factor includes: generating a simulation model based on a physical structure of the detector module; and determining the respective reference energy weighting factor corresponding to each of the plurality of depth positions of the crystal based on the generated simulation model. Determining the respective reference energy weighting factor corresponding to each of the plurality of depth positions can include: dividing the crystal into a plurality of depth levels along a depth direction of the crystal based on the simulation model; determining a reference energy weighting factor corresponding to each of the plurality of depth levels; and determining the respective reference energy weighting factor corresponding to one of the depth positions based on the determined reference energy weighting factor of a depth level including the one of the depth positions. Determining the reference energy weighting factor corresponding to each of the plurality of depth levels can include: acquiring a maximum energy output by the crystal at the depth level; acquiring a total energy output by the detector module at the depth level when the crystal outputs the maximum energy; and determining the reference energy weighting factor corresponding to the crystal at the depth level according to the maximum energy and the total energy.

In some cases, determining the associations between the plurality of depth positions of the crystal and the determined respective reference energy weighting factors can include: dividing the crystal into a plurality of levels along a depth direction; determining a reference energy weighting factor corresponding to each of the plurality of levels; and determining the associations based on the reference energy weighting factors corresponding to the plurality of levels of the crystal.

In some cases, determining the respective reference energy weighting factor includes: acquiring a maximum energy output by the crystal at the depth position; acquiring a total energy output by the detector module when the crystal outputs the maximum energy; and determining the respective reference energy weighting factor corresponding to the crystal at the depth position according to the maximum energy and the total energy. The respective reference energy weighting factor can be determined to be a ratio between the maximum energy and the total energy.

In some cases, the plurality of depth positions of the crystal includes multiple continuous depth positions, and determining the respective reference energy weighting factor can include: determining a functional relationship between the multiple continuous depth positions and corresponding reference energy weighting factors.

In some examples, determining the actual energy weighting factor includes: obtaining a maximum energy output by the crystal; obtaining an actual total energy output by the detector module when the crystal outputs the maximum energy; and determining the actual energy weighting factor of the crystal according to the maximum energy output by the hit crystal and the actual total energy output by the detector module. In some examples, the method further include: determining a plurality of single events with corresponding acting positions; and determining whether two single events constitute a coincidence event according to the corresponding acting depth positions with a coincidence determination principle.

Another innovative aspect of the subject matter described in the present disclosure can be embodied in methods that include the actions of determining a reference energy weighting factor corresponding to each of a plurality of depth positions of a crystal in a detector module; determining a correspondence between depth position and reference energy weighting factor with the determined reference energy weighting factor corresponding to each of the depth positions of the crystal in the detector module; receiving single event signals produced in the detector module, the single event signals being associated with a single event; determining a hit crystal corresponding to a maximum single event signal of the single event signals; determining an actual energy weighting factor of the hit crystal; determining an actual depth position corresponding to the actual energy weighting factor of the hit crystal, according to the correspondence between depth position and reference energy weighting factor for the hit crystal, as an acting position in the detector module for the single event; determining a response line of a coincidence event according to respective acting positions in the detector module for two single events constituting the coincidence event, the two single events including the single event; and reconstructing an image according to the response line.

The foregoing and other embodiments can each optionally include one or more of the following features, alone or in combination. The method can further include determining the reference energy weighting factor by performing a simulation modeling. In some cases, determining the correspondence between depth position and reference energy weighting factor includes: dividing the crystal in the detector module into a plurality of levels along a depth direction, and determining the correspondence between depth position and reference energy weighting factor with the reference energy weighting factor corresponding to each of the plurality of levels.

In some cases, determining the reference energy weighting factor comprises acquiring a maximum energy output by the crystal at the depth position; acquiring a total energy output by the detector module when the crystal outputs the maximum energy; and determining the reference energy weighting factor corresponding to the crystal at the depth position according to the maximum energy and the total energy.

In some cases, determining the actual energy weighting factor comprises obtaining a maximum energy output by the hit crystal; obtaining an actual total energy output by the detector module when the hit crystal outputs the maximum energy; and determining the actual energy weighting factor of the hit crystal according to the maximum energy output by the hit crystal and the actual total energy output by the detector module.

Other embodiments of these aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

A detector of a PET system may be of a ring structure. In an example, an annihilation event occurs at a center of the ring structure. A pair of gamma-photons generated by the annihilation event may be incident into a pair of crystals along opposite directions in a straight line, and gamma-rays are perpendicular to an incident plane (perpendicular to a line connecting a center of the crystal and the center of the ring structure) of any crystal of the pair of crystals. Therefore, the pair of crystals has little chance to be incident into other crystals. A response line formed between the pair of crystals may be consistent with an actual path of the gamma-rays, and therefore, the response line formed between the pair of crystals may indicate correct position information of the crystals into which the pair of gamma photons is incident.

In another example, an annihilation event may not occur at the center of the ring structure. For example, if a gamma-ray forms an acute angle with an incident plane of a first crystal, the gamma-ray may be obliquely incident into the first crystal and thus may be incident into a crystal adjacent to the first crystal or may be acted with the crystal adjacent to the first crystal when Compton scattering occurs in the first crystal. In this way, the formed response line may be inconsistent with the actual path of the gamma-ray. The quality of the reconstructed image may be undesirable and image resolution may be reduced. This phenomenon may be more significant when an annihilation position is further from the center of the ring structure. The annihilation position is a position at which an annihilation event occurs.

Figure 1:
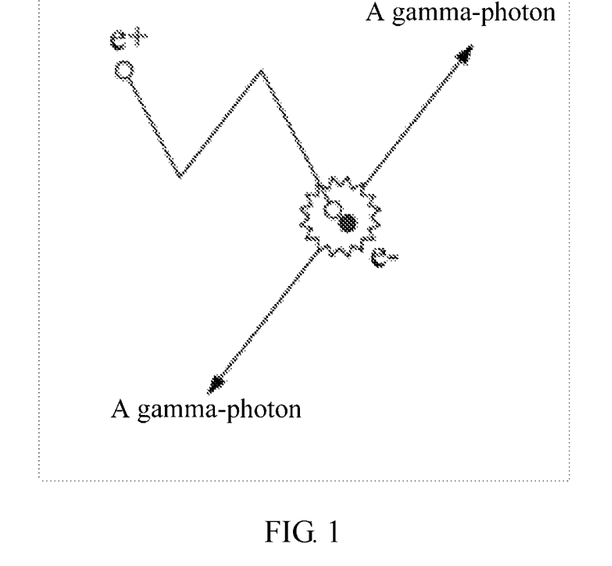
FIG. 1 is a schematic diagram of a positron annihilation event according to one or more examples of the present disclosure.

FIG. 1 is a schematic diagram of a positron annihilation event according to one or more examples of the present disclosure. For example, a Fluoro Deoxy Glucose (FDG) marker containing positron radionuclide may be injected as a tracer into a subject. After being injected into the subject, the tracer may spread into different tissues along with blood and participate in metabolism of the subject. During the process, the positron radionuclide in the tracer may release a positron e+. After moving a distance in the subject, the released positrons e+ may be annihilated with a negatron e− in the surrounding environment and then a pair of gamma-photons having equal energy (e.g., 511 KeV) and opposite propagation direction (e.g., about 180 degrees) may be generated. The pair of gamma-photons may be detected by a detector of a PET system. In this way, positron analysis may be carried out and concentration distribution of the tracer in the subject may be obtained.

Figure 2:
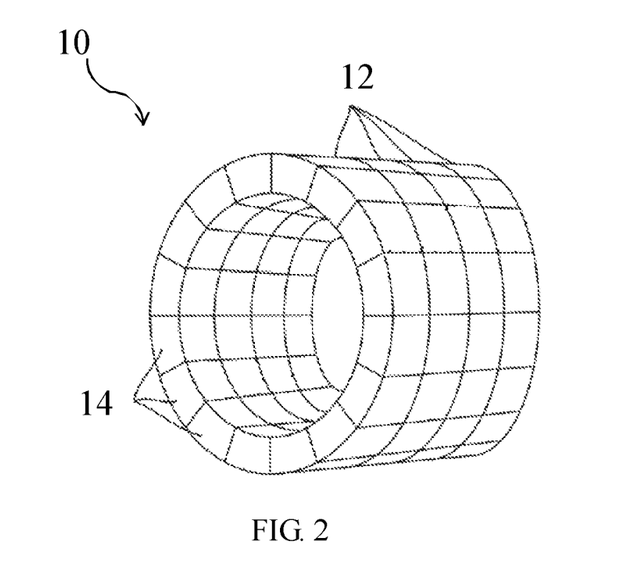
FIG. 2 is a schematic diagram of a detector of a PET system according to one or more examples of the present disclosure.

FIG. 2 is a schematic diagram of a detector 10 of the PET system according to one or more examples of the present disclosure. The detector 10 may include a plurality of detector rings 12 arranged along an axis of the detector. Each detector ring 12 may include a plurality of detector modules 14 assembled together. The plurality of detector rings 12 may constitute an internal space. A gamma-photon pair generated by a positron annihilation event which occurs in the internal space may be detected by a pair of detector modules 14 when the gamma-photon pair is incident on the pair of detector modules 14 along opposite directions.

Figure 3:
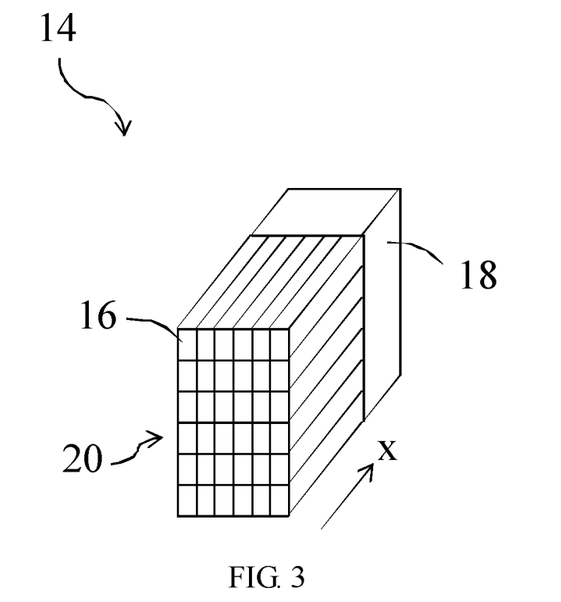
FIG. 3 is a schematic diagram of a detector module according to one or more examples of the present disclosure.

FIG. 3 is a schematic diagram of the detector module 14 according to one or more examples of the present disclosure. Each detector module 14 may include a plurality of crystals 16 and a photoelectric detecting component 18. The plurality of crystals 16 may form a crystal array 20. A crystal 16 may be a scintillation crystal. The crystal 16 may absorb a gamma-photon and produce a number of visible light signals according to the energy of the gamma-photon. Only for illustration, as shown in FIG. 3, the crystal array 20 is a 6*6 crystal array, which is not limited hereto. The crystal array 20 may be configured according to practical applications. The photoelectric detecting component 18 may include a photomultiplier to convert visible light signals produced by the crystal 16 into electrical signals to be output. The detector module 14 may include one or more photoelectric detecting components 18. The electrical signals may be used for coincidence determination, e.g., the electrical signals may be used to determine whether the time at which two gamma-photons are incident into two detector modules 14 is within a preset time window.

Figure 4A:
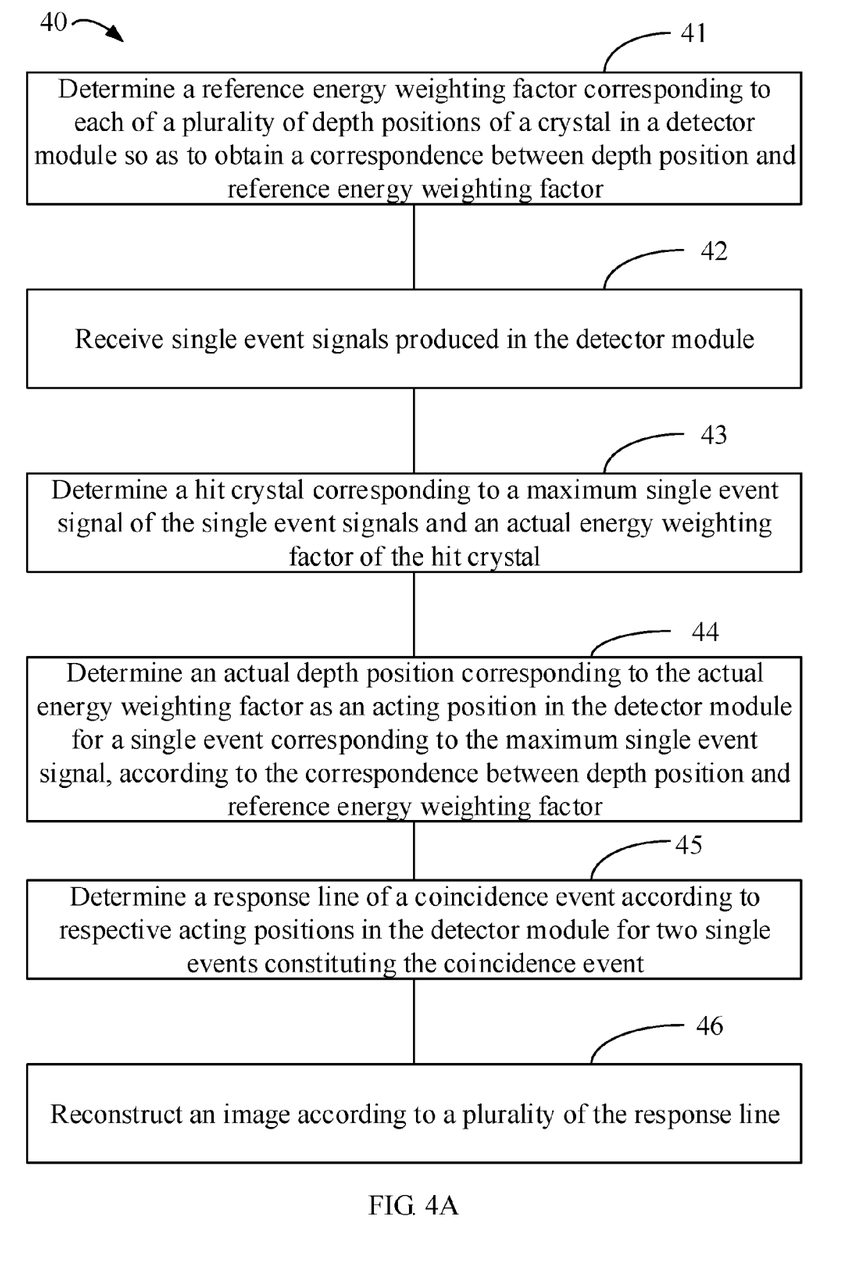
FIGS. 4A-4C are flow diagrams of processes of an imaging method according to one or more examples of the present disclosure.

FIG. 4A is a flow chart of a process 40 of an imaging method according to one or more examples of the present disclosure. The imaging method may be applied in a PET system. The process 40 may include steps 41 to 46.

At step 41, a respective reference energy weighting factor corresponding to each of a plurality of depth positions of a crystal in a detector module is determined. In such a way, correspondences (or associations) between the depth positions of the crystal and the respective reference energy weighting factors can be obtained for the crystal.

Figure 4B:
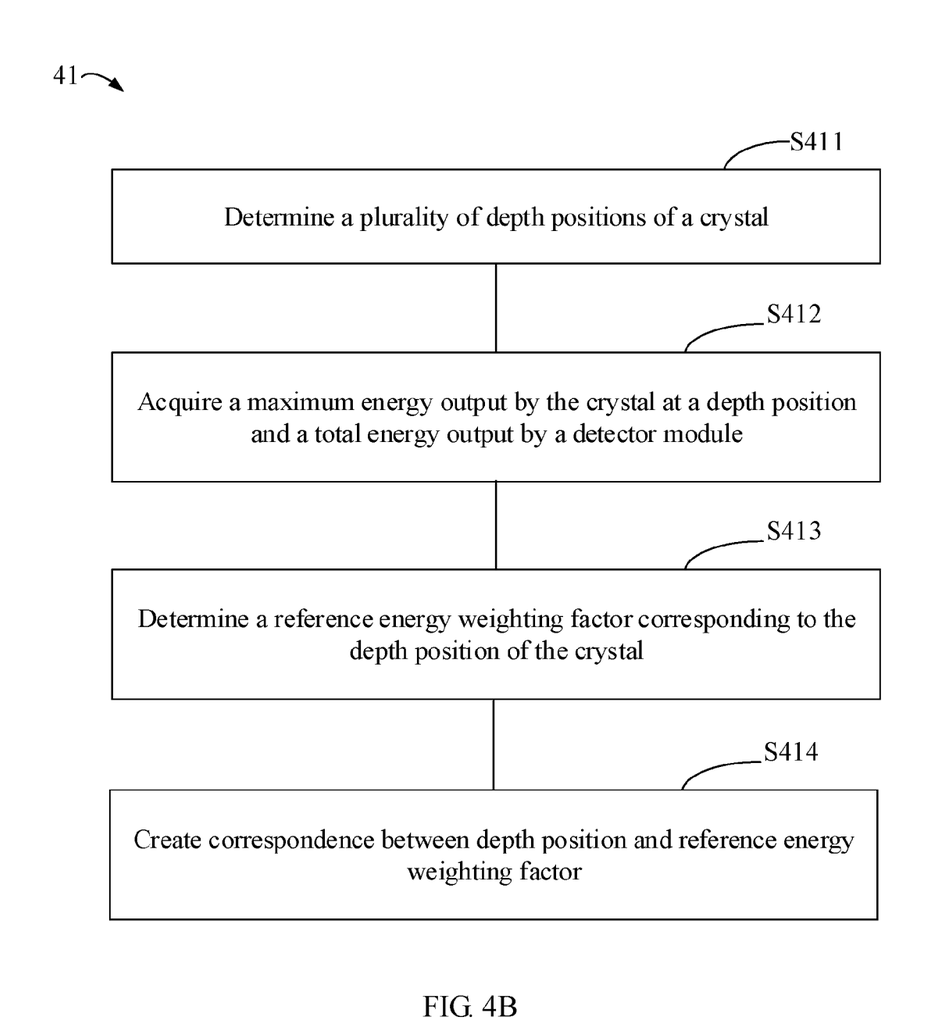

FIG. 4B is a flow chart of an example process performing step 41, which can include steps S411 to S414.

At step S411, the plurality of depth positions of the crystal are determined. A depth position of the crystal may indicate its position in a depth direction of the crystal, e.g., x direction as shown in FIG. 3.

In an example, a simulation model of the PET system may be created by a simulation software (e.g., GATE simulation software) based on a physical structure of the detector module. In an example, the physical structure of the detector module may include one or more parameters such as, structure, size, arrangement and so on for each crystal in detector module. The parameters can be entered into the simulation software to create the simulation model. Then, based on the simulation model, each crystal may be divided into a plurality of levels in the depth direction, and a reference energy weighting factor corresponding to each of the plurality of levels may be determined. It is understood that the deeper the depth of a gamma-photon incident into a crystal is, the more energy loss the gamma-photon experiences. Therefore, the reference energy weighting factor corresponding to each of the plurality of levels may be different.

In some cases, each of the plurality of levels may be equal in step length. For example, a crystal may be equally divided into N portions in the depth direction, where N is a positive integer greater than 1. For example, it is assumed that the depth of a crystal is 20 mm, and the depth may be divided into 5 levels in a step length of 4 mm, e.g., levels at depths of 0 to 4 mm, 4 mm to 8 mm, 8 mm to 12 mm, 12 mm to 16 mm, and 16 mm to 20 mm, respectively. A depth position is within one of the depth levels. For example, a depth position of 3 mm is within the first depth level of 0 to 4 mm. In some cases, for each depth position in a depth level, the reference energy weighting factor can be the same as the reference energy weighting factor for the depth level. In some cases, for a depth position in a depth level, the reference energy weighting factor can be determined based on the reference energy weighting factor for the depth level, e.g., based on a function. The smaller the step length is, the more reference energy weighting factors can be obtained for the crystal, and the higher image resolution can be achieved.

In some cases, each of the plurality of levels may not be equal in step length or not be exactly equal in step length. The depth of a crystal may not be equally divided into levels. For example, it is assumed that the depth of a crystal is 18 mm and the depth may be divided into 5 levels, where a first level is at a depth of 0 to 2 mm, and a second level to a fifth level, which may be divided in the same step length of 4 mm, are at depths of 2 mm to 6 mm, 6 mm to 10 mm, 10 mm to 14 mm, and 14 mm to 18 mm, respectively.

In some other cases, each of the plurality of levels may also be divided in accordance with a particular regulation. For example, each level may be divided in a progressively increasing or decreasing step length between the levels, which is not limited hereto. Each of the plurality of levels can also be divided according to a practical application.

In an example, multiple discrete depth positions may be selected and a respective reference energy weighting factor corresponding to each of the multiple discrete depth positions may be determined.

In another example, respective reference energy weighting factors corresponding to multiple continuous depth positions of a crystal may also be determined, e.g., a functional relationship between depth position and reference energy weighting factor for a crystal may be determined. The aforementioned plurality of depth positions may include the above multiple discrete depth positions, and may also include the above multiple continuous depth positions.

In an example, when a depth of each crystal in a crystal array is divided into the same number of levels which are equal in step length, the selected depth positions of each crystal in the crystal array may be the same. For example, a second level of the depth of each crystal in the crystal array may be selected, or the depth position of each crystal at x=8 mm in the crystal array may be selected. In another example, the selected depth positions of one or more crystals in the crystal array may be different.

At step S412, a maximum energy $E_{max}$ output by the crystal at a depth position and a total energy E output by the detector module are acquired.

In one or more examples, based on the above-described simulation model of the PET system, position information and energy information of a single event received by the detector module are obtained.

The single event may be an event that one gamma-photon is incident into one crystal. The position information indicates a position where the single event happens, and may be represented by a position of the crystal hit by the gamma-photon of the single event in the crystal array, such as a row number and a column number of the crystal hit by the gamma-photon in the crystal array. According to a design of the detector module, the position information may be obtained based on a centroid method (e.g., Anger Logic method) or based on an intensity of a signal output by the detector module (e.g., an one-to-one out system). The energy information may include the maximum energy $E_{max}$ at each depth level output by the hit crystal and the total energy E collected (or output) by the detector module when the hit crystal outputs the maximum energy $E_{max}$. The total energy E may be collected at each depth level of the hit crystal and be a sum of energy output by the whole crystal array at the depth level, e.g., output by multiple crystals including the hit crystal in the whole crystal array at the depth level. The multiple crystals are associated with the single event. The gamma-photon can be incident into each of the multiple crystals in a way that a plurality of single event signals associated with the single event are generated. One of the plurality of single event signals corresponds to one of the multiple crystals. At each depth level for the hit crystal, the maximum energy $E_{max}$ is a maximum of energy output by the multiple crystals including the hit crystal in the whole crystal array. Thus, the maximum energy output by a crystal at each depth position may be obtained. For example, the maximum energy output by a crystal at each level may be obtained. The maximum energy output by the crystal at a level can be considered as the maximum energy output by the crystal at each depth position within in the level. A virtual radioactive source (e.g., a point radioactive source) may be set in the simulation model, and it can emit a ray incident into a crystal similar to a gamma-photon which is from an annihilation event incident into a crystal. The simulation model may detect the maximum energy $E_{max}$ at each depth level and the total energy E. In this way, by the simulation model, the energy information can be obtained.

At step S413, a reference energy weighting factor corresponding to the depth position of the crystal is determined according to the maximum energy $E_{max}$ at the depth position of the crystal and the total energy E output.

In one or more examples, the reference energy weighting factor 6 is determined according to the following formula:

$$\sigma(i, j, k) = \frac{E_{max}(i, j, k)}{E}.$$

In the above formula, i and j are position information of a crystal and represent a coordinate position of the crystal in the crystal array, where i and j are positive integers greater than or equal to 1. In an example, i and j may indicate that the crystal is located in the i-th row and the j-th column in the crystal array. In an example, k may represent the k-th level of the crystal in the depth direction, and k is a positive integer greater than or equal to 1. In another example, k may represent a depth position, for example, the k-th selected depth position, which is not limited hereto.

At step S414, the correspondence between depth position and reference energy weighting factor may be created with the reference energy weighting factor, the position information and the depth position of the crystal.

In one or more examples, an energy weighting factor searching table may be created with the reference energy weighting factor, the position information and the depth position of the crystal. Each depth position of the crystal can be associated with a respective reference energy weighting factor and/or respective position information. The energy weighting factor searching table can store associations between crystals and respective position information and associations between depth positions of crystals and respective reference energy weighting factors. The operation of the step 41 may be completed offline in advance before an actual scan of the PET system, and the correspondence between depth position and reference energy weighting factor may be created in advance and stored in a storage module (or a repository) in the PET system.

According to the above examples, reference energy weighting factors may be determined by simulation modeling. Compared with determining reference energy weighting factors by a test, both workload and cost of the above method of determining reference energy weighting factors by simulation modeling may be significantly reduced.

Referring back to FIG. 4A, at step 42, single event signals produced in the detector module are received, and the single event signals are generated from one single event (or associated with the single event). In one or more examples, when the PET system performs the actual scan on the subject, the single event signals produced in the detector module may be collected.

At step 43, a hit crystal corresponding to a maximum single event signal of the single event signals and an actual energy weighting factor of the hit crystal are determined.

The hit crystal is a crystal hit by a gamma-photon for producing the maximum single event signal.

Figure 4C:
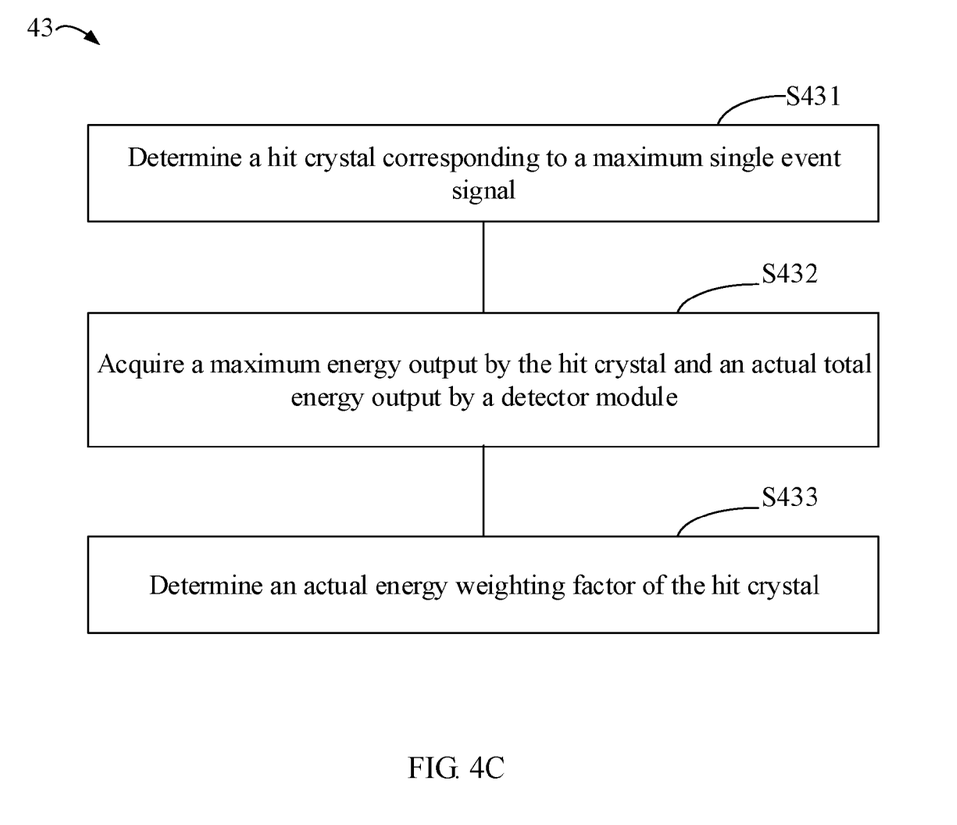

FIG. 4C is a flow chart of an example process performing step 43, which can include steps S431 to S433.

At step S431, the hit crystal corresponding to the maximum single event signal of the single event signals is determined.

The position information of a crystal corresponding to the maximum single event signal output by the detector module at a particular moment may be determined based on the centroid method or a one-to-one output system. For example, the position information of the crystal hit by the gamma-photon for producing the maximum single event signal can be determined by the one-to-one output system. The one-to-one output system means that the detector module may also include a receiving array, and the receiving array is in a one-to-one correspondence with the crystal array.

Position information of a crystal is the position of the crystal in the crystal array. In an example, when an annihilation event happens at the central position of a detector ring, a gamma-photon may be perpendicularly incident into crystal 1, and the single event signal produced in crystal 1 may be the single event signal having the maximum signal intensity among single event signals produced in the detector module at this moment. Crystal 1 may be regarded as a hit crystal in which the single event happens, e.g., a crystal hit by the gamma-photon associated with the single event.

In another example, when an annihilation event does not happen at the central position of the detector ring, a gamma-photon may be obliquely incident into one or more crystals. The first crystal into which the gamma-photon is incident among the one or more crystals may be regarded as the hit crystal, and the single event signal produced in the crystal has the maximum intensity. In some cases, the gamma-photon may pass through the first crystal and then be incident into a crystal adjacent to the first crystal, and the intensity of the single event signal is relatively low in the crystal adjacent to the first crystal. In some cases, if Compton scattering occurs in the first crystal into which the gamma photon is incident, the intensity of a signal produced by acting with the crystal adjacent to the first crystal may also be relatively low. In these cases, the crystal with which the gamma-ray acts in the crystal array of the detector module may be regarded as the first crystal, e.g., the first crystal is the hit crystal.

At step S432, the maximum energy output by the hit crystal corresponding to the maximum single event signal and the actual total energy output by the detector module are acquired. The actual total energy output by the detector module is a sum of energy output by all crystals of the crystal array when the hit crystal outputs the maximum energy.

At step S433, the actual energy weighting factor of the hit crystal is determined according to the maximum energy output by the hit crystal corresponding to the maximum single event signal and the actual total energy. Similar to the reference energy weighting factor, the actual energy weighting factor can be a ratio between the maximum energy output by the hit crystal corresponding to the maximum single event signal and the actual total energy output by the detector module.

Referring back to FIG. 4A, at step 44, an actual depth position corresponding to the actual energy weighting factor for the hit crystal is determined as an acting position in the detector module for the single event, according to the correspondence between depth position and reference energy weighting factor for the hit crystal.

A depth position corresponding to the actual energy weighting factor may be determined according to the correspondence between depth position and reference energy weighting factor created in the block 41 for the hit crystal. In one or more examples, a level corresponding to the actual energy weighting factor in the depth direction may be determined. An acting depth of the hit crystal can be determined based on the determined level. Thus, the acting position of the hit crystal for the single event may be determined based on the determined acting depth of the hit crystal.

At step 45, a response line of a coincidence event is determined according to respective acting positions in the detector module for two single events constituting the coincidence event. Each acting position represents an acting depth in a hit crystal corresponding to one of the two single events.

In one or more examples, a number of single events with corresponding acting depth position information may be output, and it may be determined whether two single events constitute a coincidence event according to the acting depth position information with a coincidence determination principle. For example, two single events with corresponding acting depth position information within a time window can constitute a coincidence event. Then, a response line of the coincidence event is determined according to the position information of a pair of crystals constituting the coincidence event and the depth positions of the gamma-photons in the crystals. In this way, the response line of an actual annihilation event may be obtained.

At step 46, an image is reconstructed according to a plurality of response lines including the response line.

The plurality of response lines of coincidence event may be determined according to the method of the steps 42 to 45. In one or more examples, an image may be reconstructed according to information of the plurality of response lines.

The operations of the imaging method 40 are illustrated in a form of steps, but the sequence of each of the steps shown in FIGS. 4A, 4B and 4C and the operations in each of the steps are not limited to the above examples. For example, the operations in each of the steps may be carried out in different sequences. The operations in one step may be combined with the operation in another step, or divided into a plurality of sub-steps.

Figure 5:
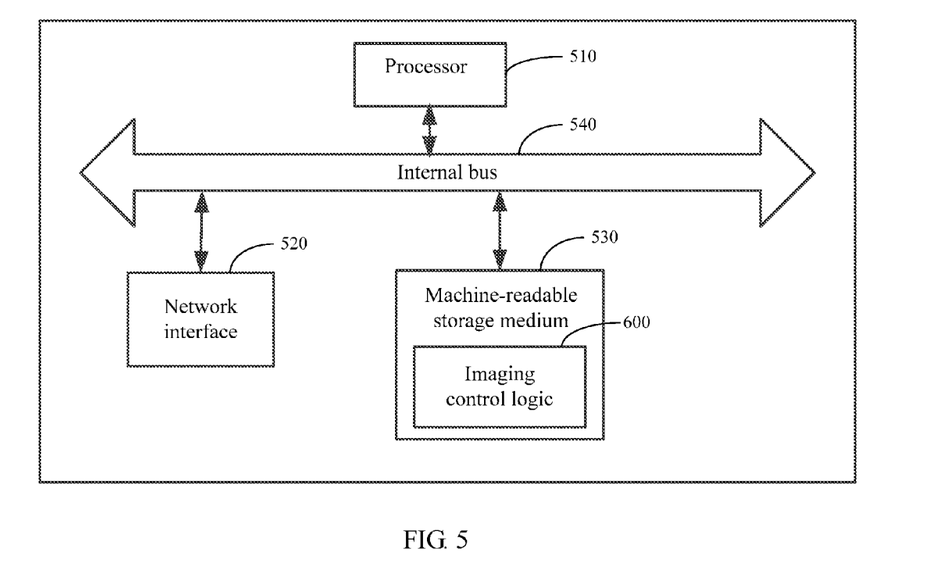
FIG. 5 is a hardware structure diagram of an imaging system according to one or more examples of the present disclosure.

Corresponding to the aforementioned examples of the imaging method, the present disclosure also provides examples of an imaging system. FIG. 5 is a hardware structure diagram of an imaging system according to one or more examples of the present disclosure. In an example, the imaging system may be a PET system. The imaging system may be implemented by software, hardware or a combination of software and hardware. From the hardware level, in addition to a processor 510, a network interface 520, a machine-readable storage medium 530 and an internal bus 540 shown in FIG. 5, the imaging system may also include other hardware according to actual functions, and further description is omitted for brevity.

In different examples, the machine-readable storage medium 530 may be a Read-Only Memory (ROM), a volatile memory, a non-volatile memory, a flash memory, a storage drive (e.g., hard disk drive), a solid state hard disk, any type of storage disk (e.g., optical disk, Digital Video Disk (DVD)), or a similar storage medium, or a combination thereof.

Figure 6:
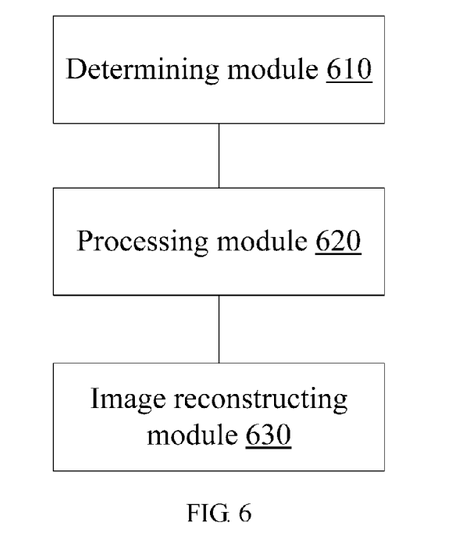
FIG. 6 is a functional module diagram of imaging control logic according to one or more examples of the present disclosure.

Further, imaging control logic 600 is stored on the machine-readable storage medium 530. As shown in FIG. 6, divided by functions, the imaging control logic 600 may include: a determining module 610, a processing module 620 and an image reconstructing module 630.

The determining module 610 may be configured to determine a reference energy weighting factor corresponding to each of a plurality of depth positions of a crystal in a detector module, and a correspondence between depth position and reference energy weighting factor with the reference energy weighting factor corresponding to each of the depth positions of the crystal in the detector module.

In one or more examples, the determining module 610 may be configured to divide the crystal in the detector module into a plurality of levels along a depth direction, and determine the correspondence between depth position and reference energy weighting factor with the reference energy weighting factor corresponding to each of the plurality of levels. The determining module 610 may be further configured to acquire a maximum energy output by the crystal at the depth position; acquire a total energy output by the detector module when the crystal outputs the maximum energy; and determine the reference energy weighting factor corresponding to the crystal at the depth position according to the maximum energy and the total energy.

In one or more examples, the determining module 610 may include a depth position determining sub-module, a reference energy weighting factor generating sub-module and a correspondence creating sub-module. The depth position determining sub-module may be configured to determine the plurality of depth positions of the crystal. In one or more examples, the depth position determining sub-module 611 may be configured to perform depth simulation modelling and divide the crystal into a plurality of levels in the depth direction based on the simulation model. In one or more examples, the depth position determining sub-module may be further configured to obtain position information and energy information of single events received at different depth positions by the detector module. In an example, the position information and the energy information of the single events may be obtained by an information identifying sub-module. The information identifying sub-module and the depth position determining sub-module are modules independent of each other.

The reference energy weighting factor generating sub-module may be configured to obtain a maximum energy $E_{max}$ output by the crystal at a depth position and a total energy E output by the detector module, and determine a reference energy weighting factor corresponding to the depth position of the crystal according to the maximum energy $E_{max}$ at the depth position of the crystal and the total energy E. In one or more examples, energy information and/or position information of the single events received at different depth positions by the detector module may be obtained by the reference energy weighting factor generating sub-module.

The correspondence creating sub-module may be configured to create the correspondence between depth position and reference energy weighting factor with the reference energy weighting factor, the position information and the depth position of the crystal.

The processing module 620 may be configured to receive single event signals produced in the detector module; determine a hit crystal corresponding to a maximum single event signal of the single event signals and an actual energy weighting factor of the hit crystal; determine an actual depth position corresponding to the actual energy weighting factor of the hit crystal, according to the correspondence between depth position and reference energy weighting factor, as an acting position in the detector module for a single event corresponding to the maximum single event signal; and determine a response line of a coincidence event according to respective acting positions in the detector module for two single events constituting the coincidence event.

Figure 7:
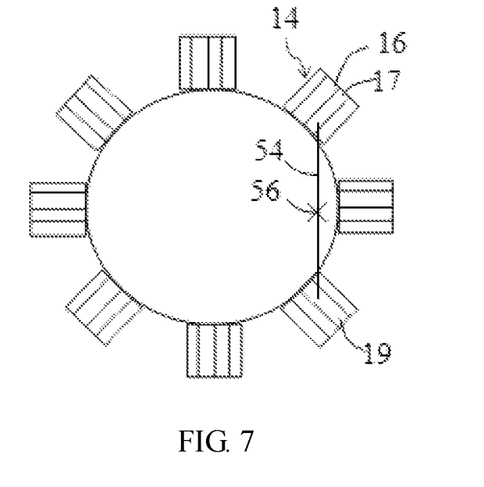
FIG. 7 is a structure diagram of a detector ring according to one or more examples of the present disclosure.

The imaging system as shown in FIG. 5 may also include a detector ring (not shown in FIG. 5), and the detector ring includes the plurality of detector modules 14. Each detector module 14 includes the plurality of crystals 16. FIG. 7 is a schematic diagram of a detector ring according to one or more examples of the present disclosure. A pair of crystals denoted by reference numerals 17 and 19 in FIG. 7 is a pair of hit crystals. The processing module 620 may be configured to perform the steps 42 to 45 of the aforementioned imaging method 40. The processing module 620 may be configured to obtain a maximum energy output by the hit crystal 17 and an actual total energy output by the detector module 14 when the hit crystal 17 outputs the maximum energy, and determine an actual energy weighting factor of the hit crystal 17 according to the maximum energy output by the hit crystal 17 and the actual total energy when the hit crystal 17 outputs the maximum energy. The processing module 620 may be further configured to obtain a maximum energy output by the hit crystal 19 and an actual total energy output by the detector module 14 when the hit crystal 19 outputs the maximum energy, and determine an actual energy weighting factor of the hit crystal 19 according to the maximum energy output by the hit crystal 19 and the actual total energy when the hit crystal 19 outputs the maximum energy.

The processing module 620 includes a data collecting module, an information identifying module, an actual energy weighting factor generating module, an energy weighting factor searching module and a coincidence determining module. The data collecting module may be configured to collect (or receive) single event signals output by the detector module during an actual scan. The information identifying module may be configured to determine the position information of the hit crystal. In one or more examples, the information identifying module may be further configured to determine energy information of the maximum energy output by the hit crystal and the actual total energy. In one or more examples, the information identifying module may include a position information identifying module for obtaining the position information and an energy information identifying module for obtaining the energy information.

The actual energy weighting factor generating module may be configured to obtain an actual energy weighting factor according to the maximum energy output by the hit crystal and the actual total energy. In one or more examples, the energy information of the maximum energy output by the hit crystal and the actual total energy may be determined by the actual energy weighting factor generating module. The energy weighting factor searching module may be configured to search for the depth position of the hit crystal corresponding to the actual energy weighting factor in the correspondence between depth position and reference energy weighting factor.

The coincidence determining module may be configured to determine whether single events happening in a pair of crystals constitute a coincidence event. If so, the line connecting the depth positions of the pair of hit crystals 17 and 19 is determined as a response line 54 of the coincidence event. The annihilation event 56 occurs on the response line 54. The image reconstructing module 630 may be configured to reconstruct an image according to a plurality of response lines.

Taking implementation by software for example, further description is made on how the imaging system executes the imaging control logic. In this example, the imaging control logic in the present disclosure should be interpreted as machine-executable instructions stored on the machine-readable storage medium 530. When the processor 510 in the imaging system of the present disclosure executes the control logic, the processor 510 may execute the above-described imaging method by invoking machine-executable instructions corresponding to the control logic stored on the machine-readable storage medium 530.

Details of the implementation process of the functions and effects of different modules in the above-described imaging control logic may be seen in the implementation process of corresponding blocks in the above-described imaging method 40, and further description is omitted for brevity.

The present disclosure further provides a machine-readable storage medium including machine-executable instructions, for example, the machine-readable storage medium 530 shown in FIG. 5. The machine executable instructions may be executed by the processor 510 in the imaging system to perform the above-described imaging method.

For the system examples, since they substantially correspond to the method examples, the correlations therebetween may refer to part of the method examples. The system examples described above are merely illustrative, wherein units described as separate components may be or may not be physically separated, and components displayed as units may be or may not be physical units, i.e., may be located in one place, or may be distributed to a plurality of network elements. Part or all of the modules may be selected according to actual requirements to achieve the purpose of the solution of the present disclosure. Those skilled in the art will understand and implement it without creative work.

The above are merely descriptions of the preferred embodiments of the present disclosure, which are not intended to limit the present disclosure. Any modifications, equivalent substitutions, improvements and the like made within the sprit and principles of the present disclosure shall all be encompassed in the scope of protection of the present disclosure.

The invention claimed is:

1. An imaging method comprising:
receiving single event signals produced in a detector module and associated with a single event;
determining a crystal in the detector module and corresponding to a maximum single event signal of the single event signals;
determining an actual energy weighting factor of the crystal;
determining an actual depth position corresponding to the actual energy weighting factor of the crystal according to associations between depth positions of the crystal and respective reference energy weighting factors for the crystal, as an acting position in the detector module for the single event;
determining a response line of a coincidence event according to respective acting positions in the detector module for two single events constituting the coincidence event, the two single events including the single event; and
reconstructing an image according to the response line.

2. The imaging method of claim 1, wherein determining the crystal comprises:
determining position information of the crystal corresponding to the maximum single event signal output by the detector module; and
determining the crystal for the single event based on the determined position information.

3. The imaging method of claim 2, wherein determining the position information of the crystal comprises:
using one of a centroid method and a one-to-one output system.

4. The imaging method of claim 1, further comprising:
determining a respective reference energy weighting factor corresponding to each of a plurality of depth positions of the crystal; and
determining the associations between the plurality of depth positions of the crystal and the determined respective reference energy weighting factors.

5. The imaging method of claim 4, further comprising:
determining, for each of a plurality of crystals in the detector module, respective associations between depth positions of the crystal and reference energy weighting factors corresponding to the depth positions of the crystal; and
storing the respective associations for the plurality of crystals in a repository.

6. The imaging method of claim 4, wherein determining the respective reference energy weighting factor comprises:
generating a simulation model based on a physical structure of the detector module; and
determining the respective reference energy weighting factor corresponding to each of the plurality of depth positions of the crystal based on the generated simulation model.

7. The imaging method of claim 6, wherein determining the respective reference energy weighting factor corresponding to each of the plurality of depth positions comprises:
dividing the crystal into a plurality of depth levels along a depth direction of the crystal based on the simulation model;
determining a reference energy weighting factor corresponding to each of the plurality of depth levels; and
determining the respective reference energy weighting factor corresponding to one of the depth positions based on the determined reference energy weighting factor of a depth level including the one of the depth positions.

8. The imaging method of claim 7, wherein determining the reference energy weighting factor corresponding to each of the plurality of depth levels comprises:
acquiring a maximum energy output by the crystal at the depth level;
acquiring a total energy output by the detector module at the depth level when the crystal outputs the maximum energy; and
determining the reference energy weighting factor corresponding to the crystal at the depth level according to the maximum energy and the total energy.

9. The imaging method of claim 4, wherein determining the associations between the plurality of depth positions of the crystal and the determined respective reference energy weighting factors comprises:
dividing the crystal into a plurality of levels along a depth direction;
determining a reference energy weighting factor corresponding to each of the plurality of levels; and
determining the associations based on the reference energy weighting factors corresponding to the plurality of levels of the crystal.

10. The imaging method of claim 4, wherein determining the respective reference energy weighting factor comprises:
acquiring a maximum energy output by the crystal at the depth position;
acquiring a total energy output by the detector module when the crystal outputs the maximum energy; and
determining the respective reference energy weighting factor corresponding to the crystal at the depth position according to the maximum energy and the total energy.

11. The imaging method of claim 10, wherein the respective reference energy weighting factor is determined to be a ratio between the maximum energy and the total energy.

12. The imaging method of claim 4, wherein the plurality of depth positions of the crystal comprises multiple continuous depth positions, and
wherein determining the respective reference energy weighting factor comprises:
determining a functional relationship between the multiple continuous depth positions and corresponding reference energy weighting factors.

13. The imaging method of claim 1, wherein determining the actual energy weighting factor comprises:
obtaining a maximum energy output by the crystal;
obtaining an actual total energy output by the detector module when the crystal outputs the maximum energy; and
determining the actual energy weighting factor of the crystal according to the maximum energy output by the hit crystal and the actual total energy output by the detector module.

14. The imaging method of claim 1, further comprising:
determining a plurality of single events with corresponding acting positions; and
determining whether two single events constitute a coincidence event according to the corresponding acting depth positions with a coincidence determination principle.

15. An imaging system comprising:
a processor; and
a machine-readable storage medium,
wherein, by reading and executing machine-executable instructions corresponding to imaging control logic stored on the machine-readable storage medium, the processor is caused to:
determine a reference energy weighting factor corresponding to each of a plurality of depth positions of a crystal in a detector module;
determine a correspondence between depth position and reference energy weighting factor with the determined reference energy weighting factor corresponding to each of the depth positions of the crystal in the detector module;
receive single event signals produced in the detector module, the single event signals being associated with a single event;
determine a hit crystal corresponding to a maximum single event signal of the single event signals;
determine an actual energy weighting factor of the hit crystal;
determine an actual depth position corresponding to the actual energy weighting factor of the hit crystal, according to the correspondence between depth position and reference energy weighting factor for the hit crystal, as an acting position in the detector module for the single event;
determine a response line of a coincidence event according to respective acting positions in the detector module for two single events constituting the coincidence event, the two single events including the single event; and
reconstruct an image according to the response line.

16. The imaging system of claim 15, wherein, when determining the reference energy weighting factor, the processor is caused by the machine-executable instructions to:
determine the reference energy weighting factor by performing a simulation modeling.

17. The imaging system of claim 15, wherein when determining the correspondence between depth position and reference energy weighting factor, the processor is caused by the machine-executable instructions to:
divide the crystal in the detector module into a plurality of levels along a depth direction, and
determine the correspondence between depth position and reference energy weighting factor with the reference energy weighting factor corresponding to each of the plurality of levels.

18. The imaging system of claim 15, wherein, when determining the reference energy weighting factor, the processor is caused by the machine-executable instructions to:
acquire a maximum energy output by the crystal at the depth position;
acquire a total energy output by the detector module when the crystal outputs the maximum energy; and
determine the reference energy weighting factor corresponding to the crystal at the depth position according to the maximum energy and the total energy.

19. The imaging system of claim 15, wherein, when determining the actual energy weighting factor, the processor is caused by the machine-executable instructions to:
obtain a maximum energy output by the hit crystal;
obtain an actual total energy output by the detector module when the hit crystal outputs the maximum energy; and
determine the actual energy weighting factor of the hit crystal according to the maximum energy output by the hit crystal and the actual total energy output by the detector module.

20. A non-transitory machine-readable storage medium storing instructions executable by one or more processors and upon such execution cause the one or more processors to perform operations comprising:
determining a respective reference energy weighting factor corresponding to each of a plurality of depth positions of each of a plurality of crystals in a detector module;
determining, for each of the plurality of crystals, correspondences between the plurality of depth positions of the crystal and the determined respective reference energy weighting factors;
receiving single event signals in the detector module, the single event signals being produced from one single event;
determining, among the plurality of crystals, a hit crystal corresponding to a maximum single event signal of the single event signals;
determining an actual energy weighting factor of the hit crystal;
determining an actual depth position corresponding to the actual energy weighting factor of the hit crystal, according to the correspondences between depth positions and reference energy weighting factors for the hit crystal, as an acting position in the detector module for the single event;

determining a response line of a coincidence event according to respective acting positions in the detector module for two single events constituting the coincidence event, the two single events including the single event; and
reconstructing an image according to the response line.

* * * * *